(12) United States Patent
Usui et al.

(10) Patent No.: US 6,815,541 B1
(45) Date of Patent: Nov. 9, 2004

(54) COPRECIPITANT AND METHOD FOR EXTRACTING NUCLEIC ACIDS

(75) Inventors: Mitsugu Usui, Abiko (JP); Mari Yamaguchi, Yokohama (JP); Motohito Kaneshima, Toride (JP); Akiji Aoki, Akiruno (JP)

(73) Assignee: Palma Bee'z Research Institute Co., Ltd., Tokyo (JP)

( * ) Notice: Subject to any disclaimer, the term of this patent is extended or adjusted under 35 U.S.C. 154(b) by 15 days.

(21) Appl. No.: 08/817,101

(22) PCT Filed: Aug. 9, 1996

(86) PCT No.: PCT/JP96/02263

§ 371 (c)(1),
(2), (4) Date: Apr. 18, 1997

(87) PCT Pub. No.: WO97/07207

PCT Pub. Date: Feb. 27, 1997

(30) Foreign Application Priority Data

Aug. 21, 1995 (JP) ............................................. 7-211862
Aug. 9, 1996 (JP) ............................................. 9-505013

(51) Int. Cl.[7] .............................................. C07H 21/00
(52) U.S. Cl. ................. 536/25.41; 536/25.4; 536/25.2; 435/91.1
(58) Field of Search ............................ 536/25.4, 25.41, 536/25.2; 435/91.1

(56) References Cited

FOREIGN PATENT DOCUMENTS

| | | | | |
|---|---|---|---|---|
| EP | 0 338 591 | 10/1989 | | |
| JP | 2-31696 | 2/1990 | | |
| JP | 6-46856 | 2/1994 | | |
| WO | WO 87/02064 | 4/1987 | ............ | C12Q/1/68 |
| WO | WO 92/00983 | 1/1992 | ............ | C07H/1/08 |
| WO | WO 95/02050 | 1/1995 | ........... | C12N/15/10 |

OTHER PUBLICATIONS

White et al. Principles of Biochemistry. Fifth Edition McGraw–Hill Book Co., New York: 1973, pp. 47–51.*

* cited by examiner

*Primary Examiner*—James O. Wilson
*Assistant Examiner*—Howard V. Owens, Jr.
(74) *Attorney, Agent, or Firm*—Arent Fox, PLLC (57) ABSTRACT

A coprecipitant and a nucleic-acid extraction method using the coprecipitant are provided. The coprecipitant has affinity to the nucleic acids, no competitive inhibition to the reverse transcription and no inhibition to the PCR reaction in case of extracting a very small amount of nucleic acids by alcoholic precipitation using isopropyl alcohol or ethanol. Further, the coprecipitant can precipitate with the nucleic acids as a visible white or blue precipitate, thereby to suppress technical errors and enhance the extraction efficiency.

A coprecipitant which acts in a process of extracting the nucleic acids by centrifugal separation from biological materials and/or test samples in the same manner as nucleic acids and has ability for precipitating as a visible white or blue precipitate when being separating and concentrating it by alcohol.

20 Claims, 2 Drawing Sheets

COPRECIPITANT AND METHOD FOR EXTRACTING NUCLEIC ACIDS

TECHNICAL FIELD

The present invention relates to a coprecipitant and a method of extracting nucleic acids using the coprecipitant. The coprecipitant acts in the same manner as nucleic acids in alcoholic treatment for collecting nucleic acids from biological materials and/or test samples such as blood, urine, medullary fluid, phlegm or sputum, semen, cells, tissue and biopsy samples. The coprecipitant can provide a visible precipitate of the nucleic acids from centrifugal separation, thereby to collect the nucleic acids with high extraction efficiency and good reproducibility.

BACKGROUND ART

Recently, the study or diagnosis using nucleic acid probes has made rapid progress. Thus, it becomes important to realize simplification of handling of the test samples and refine nucleic acids of high purity by elimination of impurities other than the nucleic acids.

For example, in case of effecting nucleic acid hybridization, if refinement of DNA samples are insufficient, protein tends to be bonded with DNA, and if the sample contains carbohydrates, DNA digestion by restriction enzyme is inhibited so that it is impossible to recognize the base sequence of the restriction enzyme and sufficient results are not obtainable. Also, in case of effecting nucleic acid hybridization using RNA samples, insufficient refinement of the RNA samples results in insufficient nucleic acid hybridization. Therefore, it is essential to refine sufficiently and previously the DNA samples in the nucleic acid hybridization or DNA digestion by restriction enzyme.

Moreover, in case of probe detection by the nonradioactive labeling method, if using test samples containing impurities, an antibody or avidin used as reagents may be bonded nonspecifically with the impurities and hence mistakes may happen in the judgment.

It is necessary to basically conduct the following four processes for preparing refined DNA or RNA: (1) lysis of cells, (2) deproteinization and decarbohydration, (3) separation and concentration and (4) washing and refinement.

(1) In the lysis of cells, lytic enzyme such as lysozyme and achromopeptidase, proteolytic enzyme such as proteinase K, and surfactants such as alkali and SDS are used to lyse the cell construction. In case of microbes such as tubercule bacillus and staphylococcus having stable cell walls, the cells may be broken physically using beads or ultrasonic waves. Optionally, together with such physical means lytic enzyme and proteolytic enzyme may be adopted or alkali and surfactants may be added.

(2) In the deproteinization and decarbohydration, extraction in accordance with the conventional phenol-chloroform method is adopted most prevalently. However, this phenol-chloroform method is unadvantageously unhandy because it is attended with strong toxicity and requires much labor. Namely, in this phenol-chloroform method, DNA exists in an aqueous liquid phase (an upper phase), and denatured protein forms a cotton-like white phase in an intermediate phase between the aqueous liquid phase and an organic liquid phase (a lower phase). Therefore, it is necessary to do such a troublesome operation as sucking up quietly the DNA phase alone by the use of a wide-mouth pipette with preventing the white phase from being sucked and then transferring the so-extracted DNA phase into a new microtube. Since the above operation takes much time and requires a great deal of skill, the reproducibility of the DNA collection tends to be degraded and moreover bulk processing is difficult.

(3) In the process of separation and concentration after the process (2), the nucleic acids (DNA or RNA) are precipitated from the aqueous liquid containing the nucleic acids using 100% isopropyl alcohol or 100% ethanol, thereby to be separated and concentrated. However, in the conventional separation and concentration method, as the salt concentration in the aqueous liquid containing the nucleic acids is relatively high, at this stage, when isopropyl alcohol (ultimate concentration: 50%) or ethanol (ultimate concentration: 70%) is added thereto, the precipitate of the nucleic acids is colorless and transparent so that it can not be recognized with eyes. Therefore, the precipitate was discarded and the nucleic acids were insufficiently collected. The efficiency and accuracy of the nucleic acid extraction depends first on the collection of the nucleic acids and coprecipitant without omission in the process of separation and concentration.

(4) In the process of washing and refinement, 70% ethanol is used usually to eliminate impurities from the separated and concentrated nucleic acids.

For simplification and efficiency of the extraction method, the phenol-chloroform method has hitherto been improved, and several methods not based on the phenol-chloroform method have been also developed to evade danger due to phenol.

For example, in case of extracting DNA from blood samples to examine HIV-1 or EB virus infective to lymphocytes, there is known a method wherein blood obtained by the heparin blood gathering is treated with Triton X-100, after the centrifugal separation thereof, guanidine isothiocyanate is added to the separated precipitate, the DNA is deposited by adding isopropanol and then the DNA is washed with ethanol. According to this method, the DNA can be extracted within 2 hours.

This method is very simple but not general because the kind of samples to be examined is limited to blood only.

Also, there is a method which uses a nucleic acid extraction column for rapid separation and extraction of nucleic acids but it is very expensive and requires a high cost. Therefore, this method is not suitable for general application.

Recently, a method utilizing bonding ability to DNA of cationic surfactants such as CTAB (cetyltrimethyl ammonium bromide) was reported as a low cost method for rapidly extracting nucleic acids (Japanese Patent Laid-open Publication No. 2-31696).

In this method, after pretreatment of cell lysis, a complex of nucleic acids and CTAB is formed by adding CTAB in an organic solvent and then the DNA and CTAB are lysed by lysing the complex in an aqueous solution having a high salt concentration and then the DNA is isolated by ethanol or isopropanol. Though this method does not use dangerous phenol, it still requires much labor for many steps of centrifugal and washing operations.

To solve this problem, the so-called agglutination partition method was already proposed (Japanese Patent Laid-open Publication No. 4-220738). This method is applicable to decantation or reversing as separation for extracting and refining rapidly and simply nucleic acids with high purity. In this method, pretreatment for eluting nucleic acids from biological materials is first conducted, and the pretreated materials become a mixture by adding a aqueous liquid and a non-hydrophilic organic liquid having a high specific gravity and containing a thixotropic thickening agent. After centrifugal separation of the mixture a non-flowable agglutinated phase in the boundary interface between the upper and lower phases is formed and the nucleic acids existing in the upper phase is extracted by separation.

On the other hand, the recent development of the polymerase chain reaction (hereinafter, referred to as "PCR") and the reverse transcription polymerase chain reaction (hereinafter, referred to as "RT-PCR") enables to amplify and detect a very small amount of nucleic acids. In the nucleic acid detection according to the PCR or RT-PCR method, a specific gene to: be examined is amplified, and DNA of the amplified gene is then detected by the agarose gel electrophoresis or hybridization method. However, reliable detection greatly depends on the efficiency of extracting nucleic acids from test samples and primers to be used in succeeding cDNA synthesis and PCR.

Especially, in the extraction of a very small amount of nucleic acids, there is needed a method wherein the nucleic acids are extracted at high purity and high yield without influence of qualitative change of sample components due to preservation condition and quantitative change of the nucleic acids with advance of disease.

Presently, a method using guanidine thiocyanate, phenol and chloroform in combination (generally called "AGPC method") is used prevalently for the extraction of nucleic acid. The most important point in extracting a very small amount of nucleic acids by this method is reliable collection of nucleic acids in alcoholic precipitation using isopropyl alcohol, ethanol or the like after deproteinization.

Generally, when the amount of nucleic acids in test samples is very small, ribosomal RNA or transfer RNA derived from various biological materials is added as a coprecipitant when precipitation operation by alcohol. In case that the nucleic acid to be precipitated is RNA, since the amplifying reaction according to PCR is carried out after transformation from the extracted RNA to DNA by the reverse transcription, there is a problem that the coprecipitant inhibits such reverse transcription. Moreover, in case of adding glycogen or the like as the coprecipitant, since these agents have low affinity to extracted nucleic acids, and the obtained precipitate will be invisible or unrecognizable, it is difficult to extract a very small amount of nucleic acids.

The present invention was conceived in view of the foregoing prior art problem and has for its object provision of a coprecipitant which, in a process of separating and concentrating nucleic acids from an aqueous liquid containing nucleic acids by precipitation of alcohol such as isopropyl alcohol, ethanol or the like, has affinity to nucleic acids, no competitive inhibition to the reverse transcription and no inhibition to PCR reaction and can provide a visible white or blue precipitate to suppress occurrence of technical errors with a sufficiently high collection yield, and method for extracting nucleic acids using the coprecipitant.

DISCLOSURE OF THE INVENTION

To solve the foregoing problems, a coprecipitant of the present invention, in extraction of nucleic acids by centrifugal separation from biological materials and/or test samples, acts in the same manner as nucleic acids and has an ability precipitating a visible white or blue precipitate when being separated and concentrated by alcohol. As the alcohol, isopropyl alcohol, ethanol or the like can be used. In the centrifugal separation using a microtube or the like, the precipitate is stuck to the bottom of the microtube.

As the coprecipitant, there can be mentioned starch, amylose or amylopectin constituting starch or derivatives thereof, which can form a precipitate having a visible white or blue color in alcoholic precipitation of nucleic acids. Preferably, the materials used as the coprecipitant of this invention are long chain glucose bonded polysaccharides, pigment modified long chain glucose bonded polysacchsrides or derivatives thereof.

There can be mentioned as examples of the long chain glucose bonded polysaccharides of the coprecipitant of the present invention soluble starch, corn starch, potato starch, potato soluble starch, wheat starch and starch azure which are kinds of starch or derivatives of starch.

It is preferred to use corn amylopectin, potato amylopectin, amylopectin anthranilate, amylopectin azure, insoluble corn amylopectin, soluble potato amylopectin, corn amylose, potato amylose and amylose azure which are compositions of starch or derivatives thereof.

As the pigments for preparing the pigment modified long chain glucose bonded polysaccharides, there can be mentioned azure. As the azure, Remazol Brilliant Blue R, Kemazol Brilliant Blue, Remazol Brilliant Blue R-$_D$-Xylan, Remazol Brilliant Violet 5R can be used.

As the aqueous solution for dissolving the coprecipitant, there can be mentioned distilled water, buffers such as T.E. buffer [generally used as a mixture of 50 mM tris (hydroxymethyl)aminoethane-hydrochloric acid buffer, pH 8.0, 0.20 mM, EDTA], and solutions of inorganic salts such as sodium chloride, potassium chloride, calcium chloride, magnesium chloride, sodium acetate, ammonium chloride, ammonium acetate and ammonium sulfate or mixtures thereof, these usually being used within the range of about 0.1 M to 10.0 M. Moreover, the concentration of the coprecipitant of the present invention is 0.5 to 100 µg/ml, preferably 5 to 50 µg/ml.

According to the first aspect of a method for extracting nucleic acids of the present invention, there is provided a method wherein the above coprecipitant is used as a coprecipitant which precipitates together with nucleic acids in a process extracting the nucleic acids, comprising the steps of: pretreatment for lysing nucleic acids from biological materials and/or test samples; deproteinization of the pretreated biological. materials and/or test samples; separating an aqueous liquid containing nucleic acids from the deproteinized biological materials and/or test samples; blending the aqueous liquid containing nucleic acids by adding alcohol thereto; and separating and concentrating the nucleic acids by centrifugal separation.

In the deproteinization process of the above method, phase separation extraction by phenol, solubilization of protein by a chaotropic agent, formation of a nucleic acid complex by cationic surfactants, capture of nucleic acids by a glass filter or capture of nucleic acids by magnetic beads can be adopted.

According to the second aspect of a method for extracting nucleic acids of the present invention, there is provided a method wherein the above coprecipitant is used as a coprecipitant which precipitates together with nucleic acids in a process extracting the nucleic acids, comprising the steps of: pretreatment for feluting nucleic acids from biological materials and/or test samples; adding an aqueous liquid and a non-hydrophllic organic liquid having a high specific gravity and containing a thixotropic thickening agent to the pretreated biological materials and/or test samples; mixing them; centrifugal separation thereof; easy separation of the upper phase containing nucleic acids by forming a non-flowable agglutinated phase in a boundary interface between the upper and lower phases; and blending the aqueous liquid containing nucleic acid by adding alcohol thereto; separating and concentrating the nucleic acids by centrifugal separation. Generally, this method of extracting nucleic acids is called an agglutination distribution method.

The biological materials and/or test samples used in the present invention include blood, urine, medullary fluid, phlegm or sputum, semen, cells, tissue, biological specimens, yeast, Eumycates or Fungus, bacteria, virus, cultured cells, etc.

As the thixotropic thickening agent for forming the agglutinated phase in a boundary interface between the upper and lower phases, there is used a thickening agent having bonding ability to contaminants such as protein or the like and dispersibility in a high specific gravity organic liquid.

Preferably, bentonite organic derivatives are used as the thixotropic thickening agent used in the present invention. The bentonite organic derivatives include organic derivatives of smectite clay, organic derivatives of hectorite clay, organic modified materials of montmorillonite clay, refined smectite clay, specially treated smectite clay, refined organic mineral clay, etc.

As the organic derivatives of smectite clay used as the thixotropic thickening agent of this invention, there can be mentioned BENTONE 27 (produced by N.L. Industries Inc., trade name of thixotrope and gelling agent), BENTONE 34 (produced by N.L. Industries Inc., trade name of thixotrope and gelling agent), BENTONE 38 (produced by N.L. Industries Inc., trade name of thixotrope and gelling agent), BENTONE SD-1 (produced by N.L. Industries Inc., trade name of thixotrope and gelling agent), BENTONE SD-2 (produced by N.L. Industries Inc., trade name of thixotrope and gelling agent), BENTONE SD-3 (produced by N.L. Industries Inc., trade name of thixotrope and gelling agent) and the like materials.

As the organic modified materials of montmorillonite clay used as the thixotropic thickening agent of this invention, there can be mentioned BENTONE 128 (produced by N.L. Industries Inc., trade name of thixotrope and gelling agent) and BENTONE 500 (produced by N.L. Industries Inc., trade name of thixotrope and gelling agent). Further, there can be mentioned MACALOID as the refined smectite clay, BENTONE EW (produced by N.L. Industries Inc., trade name of thixotrope and gelling agent) as the specially processed smectite clay, and BENTONE LT (produced by N.L. Industries Inc., trade name of thixotrope and gelling agent) as the refined organic mineral clays.

As the organic derivatives of smectite used as the thixotropic thickening agent of this invention, there can be mentioned BENTONE 34 (produced by N.L. Industries Inc., trade name of thixotrope and gelling agent), BENTONE SD-3 (produced by N.L. Industries Inc., trade name of thixotrope and gelling agent), BENTONE LT (produced by N.L. Industries Inc., trade name of thixotrope and gelling agent), BENTONE EW (produced by N.L. Industries Inc., trade name of thixotrope and gelling agent), MACALOID and the like materials.

However, the thixotropic thickening agents used in the present invention are not restricted to those mentioned above and any other agents than the above may be use if they can form the non-flowable agglutinated phase of this invention.

The high specific gravity organic liquid preferably used in the present invention is an organic liquid insoluble or low-soluble to water and having density larger than 1.05 gcm$^{-3}$.

As the high specific gravity organic liquid, there can be mentioned inorganic compounds such as carbon tetrachloride and carbon disulfide, halogen compounds such as chloroform, 1,2-dichloroethane, 1,2-dibromoethane, trichloroethylene, tetrachloroethylene, chlorobenzene, bromobenzene and o-dichlorobenzene, alcohol such as 2,2,2-trifluoro ethanol and phenol, aldehyde such as furfural, acid derivatives such as propylene carbonate and triethyl phosphate, nitro compounds such as nitromethane and nitrobenzene, and sulfur compounds such as sulfolane.

As the alcohol to be added as a stabilizer to the above high specific gravity organic liquid, there can be mentioned methanol, ethanol, 1-propanol, 2-propanol, isoamyl alcohol, 1-butanol, 2-butanol, isobutyl alcohol, cyclohexanol, ethylene glycol, 2-methoxyethanol and 2-ethoxyethanol.

As the aqueous liquid for eluting nucleic acid into the upper phase, there can be mentioned water, aqueous solution of inorganic salts such as sodium chloride, potassium chloride, calcium chloride, magnesium chloride, sodium acetate, ammonium chloride, ammonium acetate and ammonium sulfate, and aqueous solutions of organic salts such as dimethylamine hydrochloride and trimethylamine hydrochloride, these being used preferably with the concentration within the range of about 0.1 M to 10.0 M. To enhance the extraction efficiency of nucleic acids, 0.01 to 10% of proper anionic or nonionic surfactants may be added to the aqueous solution. The ratio between the high specific gravity organic liquid phase and the aqueous liquid phase is about 1:5 to 5:1. These phases are blended and then distributed into the lower high specific gravity organic liquid phase and the upper aqueous liquid phase by the agglutinated phase formed in a boundary interface therebetween by the centrifugal separation. Thereafter, the aqueous liquid phase (upper phase) is isolated by decantation.

The coprecipitant may be added solely or together with other coprecipitants at any step of the nucleic acid extraction process. For example, the coprecipitant can be added: (1) directly to the biological materials before the nucleic acid extraction or in the elution step of nucleic acids by lysing the biological materials (cell lysis); (2) in deproteinization; (3) in separating and concentrating the nucleic acid; or (4) in washing and refining the nucleic acids.

The lysis of the biological materials is that the materials are pretreated in a buffer (pH 5 to 9) containing a chelating agent, and then are usually treated with membrane lytic agents such as anionic surfactants or nonionic surfactants having a concentration within the range of about 0.1% to 10.0% (W/V) and protein denaturing agents such as guanidine thiocyanate of about 1 M to 5 M or guanidine hydrochloride of about 1 M to 5 M to lyse the cell membrane or cell wall. Optionally, lytic enzyme for lysing cell membrane or cell wall may be used for the above purpose.

As the lytic enzyme preferably used for lysig cell membrane or cell wall, there can be mentioned membrane lytic agents such as lysozyme, achromopeptidaze, lysostaphin, lyticase and mutanolysin of about 1 mg/ml to 50 mg/ml, or protein denaturing agents such as protease K, pronase, pepsin and papain of concentration of about 10 $\mu$g/ml to 20 mg/ml.

With the above pretreatment, the biological materials may be lysed in the aqueous solution containing the above chelating agent, membrane lysing agents, protein denaturing agents, etc. in which nucleic acids and various biologicalimaterials may be solubilized.

The operation for deproteinization is divided broadly into two groups. The one is a phase distribution method using phenol or thixotropic thickening agents, and the other is a protein solubilizing method.

In the phase distribution method of phenol, water-saturated phenol or buffer-saturated phenol is used for carrying out the deproteinization utilizing the protein denaturing effect thereof and the property that phenol and an aqueous solution are separated into two. phases.

In the deproteinization by a thixotropic thickening agent, a high specific gravity organic liquid or a mixture of high specific gravity organic liquids containing thixotropic thickening agents or a mixture of such organic liquids and alcohol, and an aqueous liquid for extracting nucleic acids in an upper phase are added and mixed in solubilized biological materials. Then, the mixture is subjected to centrifugal separation. In this case, the thixotropic thickening agent bonded to contaminants such as protein is gathered in an intermediate phase (boundary interface) due to the centrifugal force by the centrifugal separation and the buoyancy of the high specific gravity organic liquid.

As a result, a non-flowable agglutinated phase is formed by change of viscosity with thickening effect due to the increased concentration of the thixotropic thickening agent, deproteinization being conducted by decantation.

In the protein solubilizing method, using chaotropic ions such as iodine ion (I$^-$) or trifluoroacetic acid ion (CF$_3$COO$^-$) which are univalent anions and have a relatively large ionic radii, the deproteinization is carried out by way of increasing the solubility of hydrophobic molecules such as protein to weaken the hydrophilic bond thereof.

In the above-mentioned process (3) for separating and concentrating nucleic acids by alcohol, for example, 100% isopropanol (ultimate concentration: 50%) in the same amount or 100% ethanol (ultimate concentration: 70%) in twice the amount may be added to an aqueous solution containing nucleic acids, thereby the nucleic acids being separated and concentrated.

In the above-mentioned process (4) for washing and refining nucleic acids by alcohol, 70% ethanol, may be used to wash and refine the nucleic acids.

The present invention is effective, in particular, for extracting HCV-RNA which is nucleic acid of the virus considered to cause C-type hepatitis, liver cancer, etc.

BEST MODE FOR CARRYING OUT THE INVENTION

Hereinafter, the present invention will be described with reference to several embodiments. This invention, however, is not limited to these embodiments.

EXAMPLE 1

100 $\mu$l of a sample containing $10^1$ to $10^4$ copies/100 $\mu$l of HCV-RNA synthesized by cloning the 5'-noncoding region of C-type hepatitis virus and 10 $\mu$g of Amylopectin Azure (SIGMA Product Number A4640) as coprecipitant were added to 1.5 ml of a sterilized microtube. Further, 300 $\mu$l of Reagent I, quanidine thiocyanate; tri-sodium citrate, 2-hydrate; n-lauroylsarcosine, sodium salt; 2-mercaptoethanol; 1,4-dithiothreitol; polyinosinate, sodium salt; tris(hydroxymethyl) aminometane; ethylenediaminetetraacetic acid) (containing glycogen as a coprecipitant) of SepaGene-RV (a nucleic-acid extraction reagent produced by SANKO JUNYAKU Co., Ltd.) was added to the microtube, and the resultant system was mixed uniformly. Thereafter, 300 $\mu$l of Reagent II (sodium acetate, 3-hydrate; glycogen; amylopectin-azure) of SepaGene-RV (a nucleic acid extraction reagent produced by SANKO JUNYAKU Co., Ltd.) and 600 $\mu$l of Reagent III (chloroform; bromobenzene; Isoamylalcohol; Bentone SD-1 (thixotrope and gelling agent, N.C. Industries Inc.)) of SepaGene-RV (a nucleic acid extraction reagent produced by SANKO JUNYAKU Co., Ltd.) were further added, and the mixture in the microtube was shaken and blended vertically and violently for 10 minutes. The mixture was left at 0° C. (in ice water) for 15 minutes, then subjected to centrifugal separation at 12,000 rpm for 15 minutes (4° C.). Thereafter, the upper phase (aqueous liquid phase) containing HCV-RNA was shifted into another microtube by decantation. 100% isopropyl alcohol of the same amount as the upper phase (aqueous liquid phase) was added to the aqueous liquid containing HCV-RNA. The mixture was blended by reversing the microtube and left at −20° C. for 45 minutes to deposit HCV-RNA. Then, the system in the microtube was subjected to centrifugal separation at 12,000 rpm for 15 minutes (4° C.). After removal of the supernatant liquid, 70% ethanol was added and blended with the pellet (HCV-RNA could be recognized with eyes as a blue precipitate) sticking to the bottom of the microtube. Further, the mixture was subjected to centrifugal separation at 12,000 rpm for 10 minutes (4° C.), and the supernatant liquid was then removed (HCV-RNA can be recognized with eyes as a blue precipitate). The obtained residue was dried under reduce pressure for about 5 minutes and then dissolved in sterilized redistilled water. After the cDNA synthesis reaction using the solution, a two step PCR method was conducted. The amplified PCR product was then subjected to 2% agarose gel electrophoresis and was dyed by ethidium bromide to evaluate the extraction efficiency by recognizing the existence of specific bands. The results are shown in Table 2.

In the above cDNA synthesis reaction, Master Mix. (3.75 $\mu$l of sterilized distilled water, 2 $\mu$l of 5×first strand buffer, 2

μl of 2.5 mM dNTP mixture, 1 μl of 0.1 MDTT, 0.5 μl of 10 pmol antisens primer) prepared in advance was added to the HCR-RNA extract, and the mixture was reacted for 1 minute at 70° C. and then for 1 minute at 55° C. After rapid cooling, 0.5 μl of RNasin (produced by PROMEGA CO., LTD.) and 0.25 μl of MMLV reverse transcriptase produced by BRL CO., LTD.) were added to the mixture, and the reverse transcription was conducted for 30 minutes at 37° C. and then for 5 minutes at 95° C.

In the above two step PCR method, the first PCR was carried out by adding 2.5 μl of 10×reaction buffer, 2 μl of 2.5 mM dNTP mixture, 10.2 μl of sterilized distilled water, 0.25 μl of 10 pmol sensprimer and 5U/μl of Taq DNA polymerase (produced by TAKARA SHUZO CO., LTD.) to the whole volume (10 μl) of the synthesized cDNA and reacting the mixture for 30 cycles of 1 minute at 94° C., 1 minute at 55° C. and 1 minute at 72° C. Next, the second PCR was carried out by adding 1 μl of the first PCR product to the mixture of 5 μl of 10×reaction buffer, 1 μl of 2.5 mM DNTP mixture, 41.9 μl of sterilized distilled water, the inner 10 pmol primers (0.5 μl of sensprimer and 0.5 μl of antisensprimer) and 0.1 μl of 5U/μl Taq DNA polymerase and reacting the admixture for 30 cycles of 1 minutes at 94° C., 1 minute at 55° C. and 1 minute at 72° C. The primer used in the above PCR is a primer fixed in advance in the 5'-non-coding region of HCV-RNA.

In the HCV-RNA extraction of this embodiment, HCV-RNA could be recognized as a blue precipitate by coprecipitation with isopropyl alcohol. With respect to the extraction efficiency of this method, $10^1$ copies of synthesized HCV-RNA could be certainly extracted as shown in Table 1.

COMPARATIVE EXAMPLE 1

This experiment was conducted in the same manner as Example 1 except that the coprecipitant of the present invention (amylopectin azure) was not used. The results are shown in Table 1. In this comparative example, the nucleic acid could not be recognized with eyes in the step of separation and concentration by isopropyl alcohol.

TABLE 1

Extraction Limit Test by Serum Dilution of Synthesized HCV-RNA
Number of copies of synthesized HCV-RNA

| Method | Sample No. | $10^1$ | $10^2$ | $10^3$ | $10^4$ | Negative Control |
|---|---|---|---|---|---|---|
| Example 1 | 1 | +*1 | + | + | + | − |
|  | 2 | + | + | + | + | − |
|  | 3 | + | + | + | + | − |
| Comparative Example 1 | 1 | + | + | + | + | − |
|  | 2 | + | + | + | + | − |
|  | 3 | + | + | + | + | − |

*1+: Sample wherein bands could be recognized by the agarose gel electrophoresis

EXAMPLE 2

HCV-RNA extraction was conducted in the same manner as Example 1 except using a; 2.2 ml microtube in place of the 1.5 ml microtube and 1200μl of 100% ethanol in place of 600 μl of 100% isopropyl alcohol.

In this Example, HCV-RNA could be recognized with eyes as a blue precipitate by coprecipitation with 100% ethanol. With respect to the extraction efficiency, $10^1$ copies of HCV-RNA could be certainly extracted (Table 2).

TABLE 2

Extraction Limit Test by Serum Dilution of Synthesized HCV-RNA
Number of copies of synthesized HCV-RNA

| Method | Sample No. | $10^1$ | $10^2$ | $10^3$ | $10^4$ | Negative Control |
|---|---|---|---|---|---|---|
| Example 2 | 1 | +*1 | + | + | + | − |
|  | 2 | + | + | + | + | − |
|  | 3 | + | + | + | + | − |

*1+: Sample wherein bands could be recognized by the agarose gel electrophoresis

EXAMPLE 3

100 μl of a test sample prepared by diluting C-type hepatitis patient's serum with HCV negative and fresh human's normal serum at a diluting ratio of $10^1$ to $10^7$ times was added to a 1.5 ml sterilized microtube. 300 μl of Reagent I (containing glycogen as coprecipitant) of SepaGene-RV (a nucleic acid extracting reagent produced by SANKO JUNYAKU CO., LTD.) was added to the sample. After uniformly blending the mixture, 300 μl of Reagent II of SepaGene-RV (nucleic-acid extracting reagent produced by SANKO JUNYAKU CO., LTD.) and 600 μl of Reagent III of SepaGene-RV (a nucleic-acid extracting reagent produced by SANKO JUN'YAKU CO., LTD.) were further added, and the mixture in the mircrotube was shaken and blended vertically and violently for ten minutes. The mixture was left at 0° C. (in ice water) for 15 minutes, then subjected to centrifugal separation at 12,000 rpm for 15 minutes (4° C.), and the upper phase (aqueous liquid phase) containing HCV-RNA was shifted into another microtube by decantation. To the upper phase (aqueous liquid phase), 30 μg of Amylopectin Azure (SIGMA Product Number A4640) as coprecipitant and 600 μl of isopropyl alcohol were added, and the mixture was blended by reversing the microtube. Thereafter, the mixture was left for 45 minutes at −20° C. to deposit HCV-RNA. After centrifugal separation at 12,000 rpm for 15 minutes (4° C.), the supernatant was removed from the microtube. To the pellet (HCV-RNA could be recognized with eyes as a blue precipitate) sticking to the bottom of the microtube, 70% ethanol was added and mixed therewith. After further centrifugal separation at 12,000 rpm for 10 minutes (4° C.), the supernatant was removed (HCV-RNA could be recognized with eyes as a blue precipitate). Next, the obtained residue was dried under reduced pressure for about 5 minutes and dissolved in sterilized redistilled water. Using the obtained solution, cDNA synthesis reaction was conducted in the same manner as in Example 1. Thereafter, the two step PCR method was conducted. The amplified PCR product was subjected to 2% agarose gel electrophoresis, and then dyed with etidium bromide to evaluate the extraction efficiency by the existence of specific bands.

In this embodiment, HCV-RNA could be recognized with eyes as a blue precipitate by coprecipitation with isopropyl alcohol. Further, with respect to the extraction efficiency, HCV-RNA could be certainly extracted from the $10^5$ times diluted serum (Table 3).

TABLE 3

Extraction Limit Test using C-type hepatitis patient's diluted serum
Diluting ratio of HCV patient's serum

| Method | Sample No. | $10^1$ | $10^2$ | $10^3$ | $10^4$ | $10^5$ | $10^6$ | $10^7$ | Negative Control |
|---|---|---|---|---|---|---|---|---|---|
| Example 3 | 1 | +*1 | + | + | + | + | −*2 | − | − |
|  | 2 | + | + | + | + | + | − | − | − |
|  | 3 | + | + | + | + | + | − | − | − |

*1+: Sample wherein bands could be recognized by the agarose gel electrophoresis
*2−: Sample wherein no band could be recognized by the agarose gel electrophoresis

EXAMPLE 4

HCV-RNA extraction was conducted using the same HCV-RNA patient's serum in the same manner as Example 1 except using a 2.2 ml microtube in place of the 1.5 ml microtube and 1200 μl of 100% ethanol in place of 600 μl of 100% isopropyl alcohol.

In this Example, HCV-RNA could be recognized with eyes as a blue precipitate by coprecipitation with 100% ethanol. With respect to the extraction efficiency, HCV-RNA could be certainly extracted from the 105 times diluted patient's serum (Table 4).

TABLE 4

Extraction Limit Test using diluted C-type hepatitis patient's serum
Diluting ratio of HCV patient's serum

| Method | Sample No. | $10^1$ | $10^2$ | $10^3$ | $10^4$ | $10^5$ | $10^6$ | $10^7$ | Negative Control |
|---|---|---|---|---|---|---|---|---|---|
| Example 4 | 1 | +*1 | + | + | + | + | −*2 | − | − |
|  | 2 | + | + | + | + | + | − | − | − |
|  | 3 | + | + | + | + | + | − | − | − |

*1+: Sample wherein bands could be recognized by the agarose gel electrophoresis
*2−: Sample wherein no band could be recognized by the agarose gel electrophoresis

EXAMPLE 5

In this experiment, a coprecipitant of the present invention was added to the known AGPC method. 100 μl of a test sample prepared by diluting C-type hepatitis patient's serum with HCV negative and fresh human's normal serum at a diluting ratio of $10^1$ to $10^7$ times was added to a 1.5 ml sterilized microtube. 200 μl of a solution (4M guanidine thiocyanate, 2-mercaptoethanol) and 5 μl of yeast-derived tRNA (4 mg/ml) as coprecipitant were added and dissolved in the sample. Further, 200 μl of water-saturated phenol, 17 μl of 2M sodium acetate and 40 μl of chloroform-isoiamyl alcohol (49:1) were added and blended therein. After the mixture was left at 4° C. for 15 minutes, then subjected to centrifugal separation at 12,000 rpm for 15 minutes (4° C.), and the upper phase (aqueous liquid phase) containing HCV-RNA was shifted into another microtube. To the upper phase (aqueous liquid phase), the same volume as the mixture of 100% isopropyl alcohol was added, and the mixture was blended by reversing the microtube. Thereafter, the mixture was left over night at −20° C. to deposit HCV-RNA. After centrifugal separation at 12,000 rpm for 15 minutes (4° C.), the supernatant was removed from the microtube. To the pellet sticking to the bottom of the microtube, 30 μg of Amylopectin Azure (SIGMA Product Number A 4640) and 70% ethanol were added and blended therewith. After centrifugal separation at 12,000 rpm for 10 minutes (4° C.), the supernatant was removed (HCV-RNA could be recognized with eyes as a blue precipitate). Next, the obtained residue was dried under reduce pressure for about 5 minutes (at room temperature) and then dissolved with sterilized redistilled water. Using the obtained solution, cDNA synthesis reaction and the two step PCR method were conducted in the same manner as in Example 1. The amplified PCR product was subjected to 2% agarose gel-lelectrophoresis.

In this embodiment, HCV-RNA could be recognized with eyes as a blue precipitate by coprecipitation with isopropyl alcohol. Further, with respect to the extraction efficiency, the result was equal to or better than the AGPC method of Comparative Example 2 (Table 5).

COMPARATIVE EXAMPLE 2

HCV-RNA extraction was conducted under the same condition as in Example 5 except that the coprecipitant (Amylopectin Azure) was not used. The results are shown in Table 5. In this case, the precipitate could not be recognized with eyes.

TABLE 6

Extraction Limit Test using diluted C-type hepatitis patient's serum
Diluting ratio of HCV patient's serum

| Method | Sample No. | $10^1$ | $10^2$ | $10^3$ | $10^4$ | $10^5$ | $10^6$ | $10^7$ | Negative Control |
|---|---|---|---|---|---|---|---|---|---|
| Example 5 | 1 | +*1 | + | + | + | + | −*2 | − | − |
|  | 2 | + | + | + | + | + | − | − | − |
|  | 3 | + | + | + | + | − | − | − | − |
| Comparative-Example 2 | 1 | + | + | + | + | − | − | − | − |
|  | 2 | + | + | + | − | − | − | − | − |
|  | 3 | + | + | + | − | − | − | − | − |

*1+: Sample wherein bands could be recognized by the agarose gel electrophoresis
*2−: Sample wherein no band could be recognized by the agarose gel electrophoresis

EXAMPLE 6

HCV-RNA extraction was conducted in the same manner as Example 5 except that amylopectin was used in place of amylopectin azure. HCV-RNA was deposited as a white precipitate from separation and concentration using 100% isopropyl alcohol. The extraction efficiency was equal to Example 5.

Next, operation of the method of the present invention is described with reference to the accompanying drawings.

Figure 1:
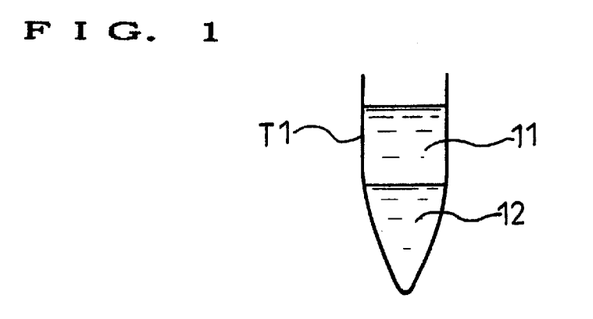
FIG. 1 shows the first step of the procedure for separating an aqueous liquid phase containing nucleic acids by the reversing separation method according to the present invention, in which the upper and lower phases are separated in a microtube.

FIG. 1 shows a state where an aqueous solution 11 in which nucleic acids and impurities other than the nucleic acids produced by denaturing protein contaminants and lysis of a biological material are dispersing, and a high specific gravity organic liquid 12 or a mixture 12 of high specific gravity organic liquids or a mixture 12 of these high specific organic gravity liquids and alcohol are separated in a microtube T1. The high specific gravity organic liquid contains a thixotropic thickening agent which has bonding ability to the contaminants in the biological material to form a non-flowable agglutinated phase in an interface between the upper and lower phases in the phase distributing extraction, thereby enabling isolation of the nucleic acid by decantation or reversing separation.

Figure 2:
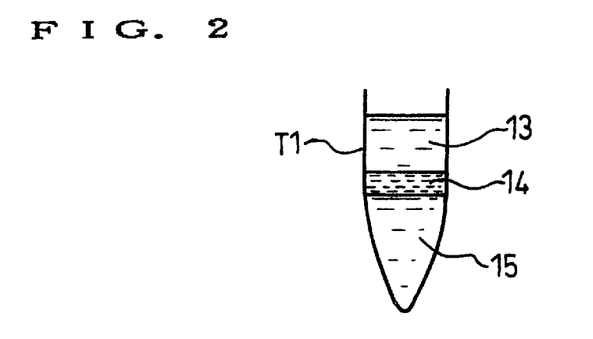
FIG. 2 shows the second step of the procedure for separating the aqueous liquid phase containing the nucleic acids by the reversing separation method according to the present invention, in which a non-flowable agglutinated phase is formed in the interface between the upper and lower phases in a microtube.

FIG. 2 shows a state where an upper phase 13 of an aqueous liquid containing DNA, a non-flowable agglutinated phase 14 and a lower phase 15 of a high specific gravity organic liquid containing contaminants such as protein, a mixture of the specific gravity organic liquid or a mixture of these high specific gravity organic liquid and alcohol are separated in the microtube. The non-flowable agglutinated phase 14 is formed by the change of viscosity resulting from increased thickening effect on the ground that the thixotropic thickening agent bonded to protein or the like is gathered in the intermediate phase (boundary interface) by the centrifugal force of centrifugal separation and buoyancy in the high specific organic liquid, the concentration of the thixotropic agent being increased.

Figure 3:
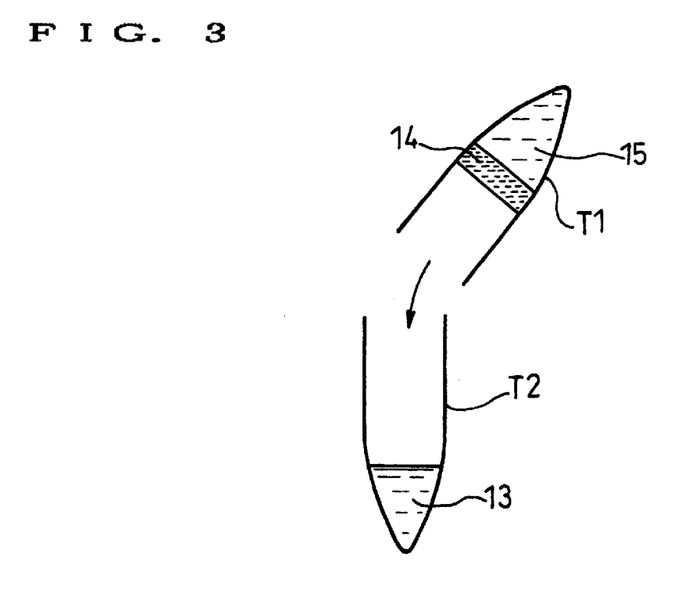
FIG. 3 shows the third step of the procedure for separating the aqueous liquid phase containing the nucleic acids by the reversing separation method according to the present invention, in which the upper phase is shifted into a new microtube by the reversing separation method.

FIG. 3 shows, a state where the upper phase 13 of an aqueous liquid containing DNA is shifted to a new microtube T2 by decantation.

Figure 4:
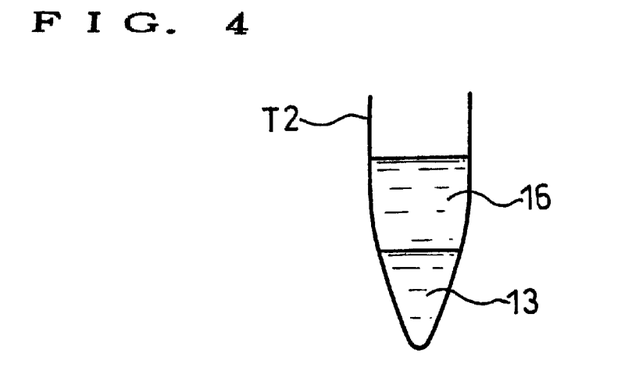
FIG. 4 shows the fourth step of the procedure for separating and concentrating the aqueous liquid phase containing the nucleic acids according to the present invention, in which alcohol is added to the aqueous liquid containing nucleic acids.
Figure 5:
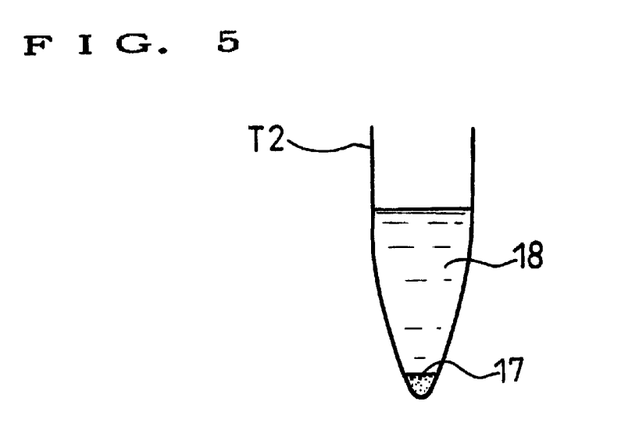
FIG. 5 shows the fifth step of the procedure for separating and concentrating the aqueous liquid phase containing the nucleic acids according to the present invention, in which a precipitate of a coprecipitant and the nucleic acids is formed.
Figure 6:
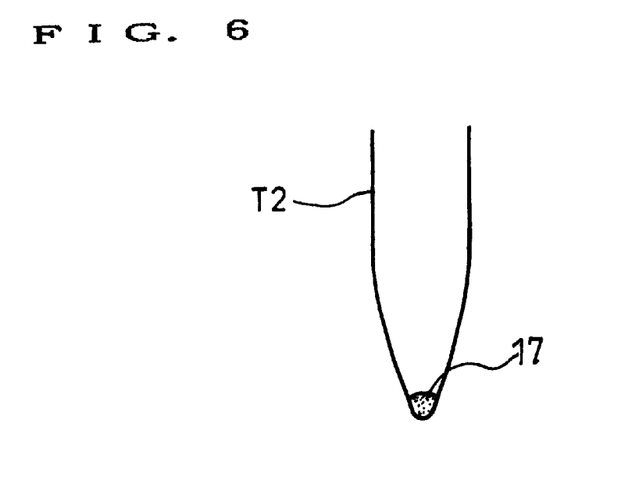
FIG. 6 shows the sixth step of the procedure for separating and concentrating the aqueous liquid phase containing the nucleic acids according to the present invention, in which a blended liquid is removed from the state shown in FIG. 5.

FIG. 4 shows a state where alcohol 16 is added to the aqueous liquid 13 containing nucleic acids (DNA), which was shifted to the microtube T2. In FIG. 4, both the alcohol and the aqueous liquid are blended to form a blended liquid 18. After the blended liquid 18 is subjected to centrifugal separation, a colored precipitate (a coprecipitant+nucleic acids) 17 is stuck to the bottom of the microtube T2 as shown in FIG. 5. FIG. 6 shows a state where the blended liquid 18 is discarded and only the colored precipitate 17 remains in the microtube T2. In the above operation, the coprecipitant of the present invention may be added at any step of FIGS. 1 to 5.

CAPABILITY OF EXPLOITATION IN INDUSTRY

According to the present invention, a very small amount of HCV-RNA in a test sample can be certainly extracted by adding a coprecipitant at any step in the extraction operation. Further, the existence of HCV-RNA can be recognized with eyes as a blue precipitate by the coprecipitation with isopropyl alcohol or ethanol. Therefore, conventional technical errors having been associated with the extraction operation can be suppressed to the minimum.

The present invention is not limited to the use of Sepa-Gene (a nucleic-acid extracting reagent produced by SANKO JUN'YAKU CO., LTD.). Further, also in the other extraction methods including AGPC method described above as the control, it is possible to recognize with eyes the existence of HCV-RNA as a blue precipitate produced by the coprecipitation with isopropyl alcohol or ethanol.

As the coprecipitant of the present invention acts in the same manner as HCV-RNA in any step of the HCV-RNA extraction operation, the extraction efficiency can be enhanced.

The coprecipitant of the present invention is not competitive with the reverse transcription or PCR reaction and/or does not inhibit these reactions, thereby exerting no effect on the detection sensitivity based on these reactions.

According to the method of this invention, as a non-flowable agglutinated phase is formed at a boundary interface between the upper and lower phases, the boundary interface becomes clear and further the upper phase of the aqueous liquid containing nucleic acids can be separated easily by decantation.

What is claimed is:

1. A method for enhancing the precipitation of nucleic acids from a biological sample, comprising the steps of:
    a) adding at least one coprecipitant which precipitates together with nucleic acids as a visible white or blue precipitate when separating and concentrating the nucleic acids by alcohol in a process of extracting with nucleic acids as a visible blue precipitate when separating and concentrating the nucleic acids by alcohol in a process of extracting the nucleic acids, at any of steps b–g;
    b) pretreating for lysing nucleic acids from biological sample;
    c) adding an aqueous liquid and a non-hydrophilic organic liquid having a high specific gravity and containing a thixotropic thickening agent to the pretreated biological sample;
    d) mixing the materials of c);
    e) centrifugal separation thereof;
    f) separating the upper phase containing nucleic acids by forming a non-flowable agglutinated phase i n a boundary interface between the upper and lower phases;
    g) blending the aqueous liquid containing nucleic acids by adding alcohol thereto; and
    h) separating and concentrating the nucleic acids together with said coprecipitant by centrifugal separation, such that a visible white or blue precipitate results.

2. The method of claim 1, wherein the coprecipitant is a composition selected from the group consisting of a long chain glucose bonded polysaccharide and a pigment-modified long chain glucose bonded polysaccharide.

3. The method of claim 1, wherein the coprecipitant is a composition comprising one or more kinds of starch selected from the group consisting of soluble starch, corn starch, potato starch, potato soluble starch, wheat starch, starch azure, corn amylopectin, potato amylopectin, amylopectin anthranilate, amylopectin azure, insoluble corn amylopectin, soluble potato amylopectin, corn amylose, potato amylose, and amylose azure.

4. A method according to claim 3, wherein said at least one coprecipitant is selected from the group consisting of starch azure, amylopectin azure and amylose azure, and said precipitate in step (h), is blue.

5. The method of claim 1, wherein the alcohol is isopropyl or ethanol.

6. The method of claim 1, wherein the nucleic acids are HCV-RNA.

7. The method of claim 1, wherein the concentration of the coprecipitant is 0.5 to 100 $\mu$g/ml.

8. A method for detecting nucleic acids during treatment to prepare refined nucleic acid from a biological sample, comprising:
    (a) contacting a biological sample containing nucleic acids with a coprecipitant at a time during a treatment to prepare refined said nucleic acids prior to or during step (b), said coprecipitant comprising at least one compound selected from the group consisting of starch azure, amylopectin azure and amylose azure, soluble starch, corn starch, potato starch, potato soluble starch, wheat starch, corn amylopectin, potato amylopectin, amylopectin anthranilate, insoluble corn amylopectin, soluble potato amylopectin, corn amylose, and potato amylose,
    (b) precipitating said biological sample and coprecipitant by adding alcohol, and
    (c) visibly detecting a blue or white precipitate to indicate the presence of said nucleic acid and coprecipitant.

9. A method according to claim 8, wherein said at least one coprecipitant is selected from the group consisting of starch azure, amylopectin azure and amylose azure, and said precipitate in step (c), is blue.

10. A method according to claim 8, wherein said alcohol is isopropyl alcohol or ethanol.

11. A method according to claim 8, wherein the nucleic acids are HCV-RNA.

12. A method according to claim 8, wherein the concentration of said coprecipitant is 0.5 to 100 µg/ml.

13. A method according to claim 8, wherein said precipitate is facilitated by centrifuging.

14. A method according to claim 8, wherein said treatment to prepare refined nucleic acids, comprises prior to step (b) performing the steps of (i) lysing, and (ii) deproteinizing said biological sample.

15. The method according to claim 14, wherein the step of deproteinizing comprises the steps: phase separation and extraction by phenol, solubilization of protein by a chaotropic agent, formation of nucleic acid complex by a cationic surfactant, and capture of nucleic acids by a glass filter or capture of nucleic acids by magnetic beads.

16. A method according to claim 14, further comprising after performing step (b), washing, and further refining said nucleic acid.

17. A method according to claim 14, wherein said at least one coprecipitant is selected from the group consisting of starch azure, amylopectin azure and amylose azure, and said precipitate in step (b) is blue.

18. A method according to claim 8, wherein said treatment to prepare refined nucleic acid comprises, prior to step (b)

(i) eluting nucleic acids from biological sample;

(ii) mixing an aqueous liquid, a non-hydrophilic organic liquid having a high specific gravity, a thixotropic thickening agent, and the eluted biological sample, and (iii) centrifuging and separating an upper phase containing nucleic acids by forming a non-flowable agglutinated phase in a boundary interface between said upper phase and a lower phase.

19. A method according to claim 18, wherein said at least one coprecipitant is selected from the group consisting of starch azure, amylopectin azure and amylose azure, and said precipitate in step (c), is blue.

20. A method according to claim 18, wherein said precipitate is facilitated by centrifuging.

* * * * *